Figure 1:
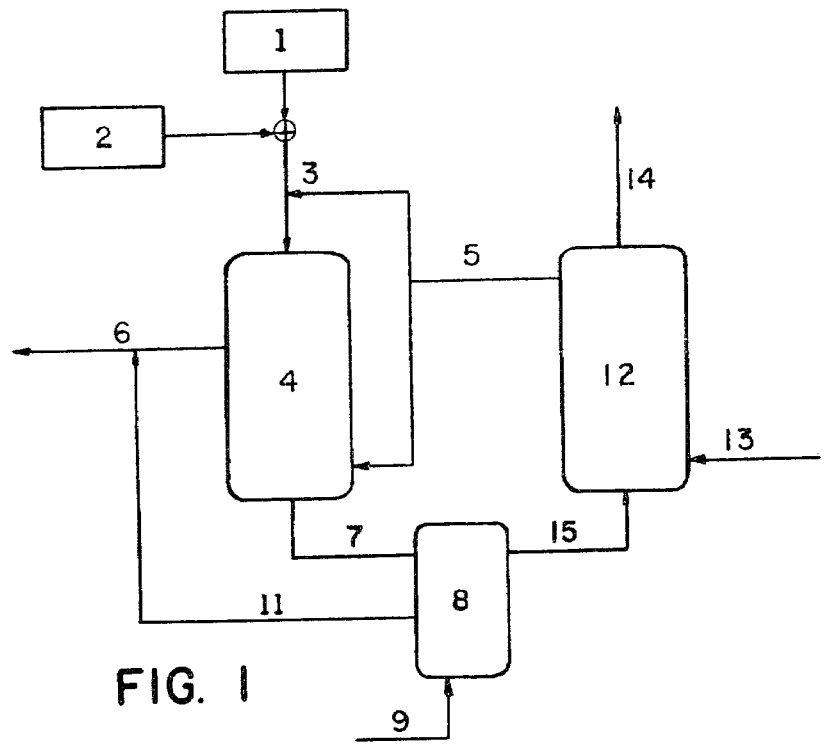

United States Patent [19]

Coutinho et al.

[11] 4,251,677

[45] Feb. 17, 1981

[54] PROCESS FOR OBTAINING GASEOUS STREAMS RICH IN ETHENE

[75] Inventors: Paulo H. D. A. Coutinho; Julio A. R. Cabral, both of Rio de Janeiro, Brazil

[73] Assignee: Petroleo Brasileiro S.A. - Petrobras, Rio de Janeiro, Brazil

[21] Appl. No.: 64,167

[22] Filed: Aug. 6, 1979

[30] Foreign Application Priority Data

Nov. 14, 1978 [BR] Brazil .................................. 7807475

[51] Int. Cl.$^3$ ................................................ C07C 1/00
[52] U.S. Cl. ...................................... 585/639; 585/640; 585/651
[58] Field of Search ................... 585/639, 640, 651

[56] References Cited

U.S. PATENT DOCUMENTS

| 3,267,023 | 8/1966 | Miale et al. | 585/639 |
| 4,156,698 | 5/1979 | Dwyer et al. | 585/640 |
| 4,172,856 | 10/1979 | Spencer et al. | 585/640 |

*Primary Examiner*—Curtis R. Davis
*Attorney, Agent, or Firm*—Norbert P. Holler; Alfred H. Hemingway

[57] ABSTRACT

This invention relates to the production of ethene with a highly profitable yield by means of fluidized bed catalytic cracking of a mixture containing 0.13 to 50 parts by weight of ethanol to 100 parts by weight of hydrocarbons blend at a temperature between 430° C. and 550° C., and pressure between 0 and 5.0kg/cm$^2$ gauge in such way that the final gaseous product resulting therefrom has en ethene content between 18.8% and 64% by volume.

15 Claims, 2 Drawing Figures

PROCESS FOR OBTAINING GASEOUS STREAMS RICH IN ETHENE

The invention concerns a process for production of ethene with commercially profitable yield, by a catalytic fluid bed cracking of a blend of gasoil and ethanol.

Ethene is valuable as a raw material for the modern petrochemical industry, not only for preparing several types of polyethylene but as well for the synthesis of many materials such as vinyl chloride, vinylidene chloride, ethyl benzene, styrene, vinyl acetate, ethylene oxide, acetic anhydride, pentaerythritol, olefins, alkylbenzenes etc., which are raw materials for obtaining polymers and other organic materials, indispensable for a modern society.

For such reasons it is important to develop means for the preparation of ethene from as many sources as possible, which would afford a constant supply to chemical industries requiring that material.

As to the actual state of art, one of the processes most employed by the industry to manufacture ethene is the pyrolysis of crude oil. However, with the continuous increase of world market price of naphtha and also due to the constant reduction of its availability, the ethene manufacturers turned to methods which involve pyrolysis of gasoils (which are liquid mixtures of hydrocarbons boiling in the temperature range from 200° C. to 600° C.) and heavier petroleum cuts, including crude oil. Such methods, however, produce gases with a very low ethene content and require cumbersome and costly procedures in order to obtain ethene with the convenient concentration and purity for employment by the petrochemical industry.

Catalytic cracking of gasoils, which is performed in order to produce gasoline, yields gaseous streams having a maximum content of 15% of ethene, by volume. In that case, the techniques for separation of ethene are very costly, which is the reason why the obtained gas is not commonly used as an ethene source but as a fuel gas.

According to the present invention, it was found that it is possible to obtain high ethene yields from the gaseous products if ethanol is added to the liquid blends of hydrocarbons before performing the catalytic cracking. While the "fuel gas" stream produced from the catalytic cracking of crude oil heavy cuts has an ethene content between 7 and 15% (or, calculating on $N_2$, CO and $CO_2$ free basis, between 8.8 and 18.8%), the gaseous stream resulting from the catalytic cracking of heavy crude oil cuts containing ethanol provides ethene contents from 18.8% to 64% (based on gases free of $N_2$, CO and $CO_2$) using the same conventional process, equipment and catalysts.

Figure 2:
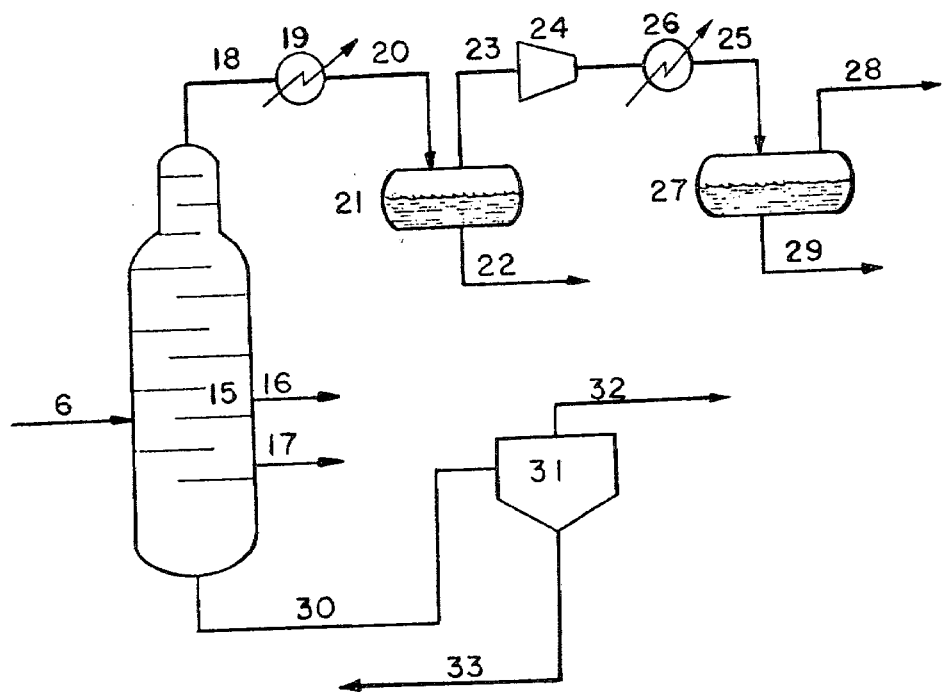

FIGS. 1 and 2 (attached) show to those skilled in the art a simplified flow sheet of the performance of this invention. Equipments and operating sequences shown here are not limitative, allowing for changes due to the available equipment, it is necessary to note that the process is intended to be put into practice with whatever equipment operates the cracking with granulated catalyst in a fluidized bed, the purification of products being made according to the usual petroleum refining techniques.

In FIG. 1 we see the operating scheme of a fluidized bed catalytic cracking and in FIG. 2, the separation of the resulting main products. A brief description of the operation and equipment lay-out follows:

(a) ethanol from a supply source (1) and gasoil from a source (2) are mixed in a point of the line (3) where the feeding rate of ethanol is adjusted in relation to that of gasoil in order to provide a constant proportion of the components; it is possible to admit a stream of heated regenerated catalyst to the mixture in a point of the line (3) before entering into the reactor (4) or, alternatively, the mixture can be admitted directly to the reactor (4) where a fluidized bed catalyst at the reaction temperature is already present;

(b) the cracking reaction product flows out of the reactor (4) through the line (6);

(c) the catalyst, coming from the regenerator (12), free of carbon deposits on its surface and conveniently heated, is introduced through the line (5);

(d) the catalyst used in the process, whose activity to promote the reaction has been reduced due to the carbon build-up over its surface, leaves the reactor through the line (7), this catalyst being the so called "spent catalyst;"

(e) the spent catalyst from the reactor (4) passes through the line (7) to the stripper (8) where it receives steam from the line (9), the products, which were absorbed by the catalyst particles are withdrawn through the line (11) and the catalyst containing carbon on its surface is withdrawn through the line (15) together with the residue which is burnt;

(f) the product entrained through the line (11) meets, in a point of the line (6), a stream of cracking products coming from the reactor (4);

(g) the spent catalyst which flows through the line (15) enters the regenerator (12) where it receives the regenerating fluid (13) which will promote the burning of the carbon accumulated on the surface of the particles of said catalyst, the flue gases (namely, final combustion products, specially $CO_2$) leaves through the line (14) and the carbon free catalyst, heated to a temperature sufficient to promote the catalytic reaction, is conducted through the line (5) to the reactor (4) where it is introduced.

FIG. 2 shows the purification steps of the catalytic cracking product. Effluent from the reactor (4) plus the product which arrives through the piping (11) are sent through the line (6) to the distillation tower (15) where they are split by fractionation into four distinct streams:

(a) a product so-called "light recycle oil", distilling in a temperature range above that of gasoline, which is withdrawn through the line (16);

(b) a product so-called "heavy recycle oil", distilling in a range above that of the light recycle oil wich leaves the tower through the line (17);

(c) a residual product which is not split up by heating, is withdrawn through the line (3) passing to a settler (31) where it is divided into a settled oil which is removed through the pipe (32) and a heavy residue which is withdrawn through the line (33) and sent to the cracking reactor (4) by means not shown in the figure;

(d) a blend of low boiling components which leaves the top of the fractionation column through the line (18) passing through the condenser (19) to the accumulating vessel (21) through the line (20).

Material contained in the accumalating vessel (21) is, in its turn, split in two fractions:

I. a liquid portion which constitutes gasoline and is withdrawn by the line (22);

II. a gaseous portion which is sent through the line (23) to the compressor (24) where it is compressed and sent to the condenser (26) and thereafter to the accumulator (27) through the line (25).

In the accumulating vessel (27) two fractions are found:

III. the liquid portion which forms the blend of light products called liquefied petroleum gases (formed by 3 to 4 carbon atoms hydrocarbons) which is removed through the line (29);

IV. the gaseous portion (containing ethene mixed with methane, hydrogen etc.) which is designated as fuel gas and is withdrawn through the line (28).

As was shown above, these schemes involve conventional operations. The separating and purification steps can be performed using methods well known by those skilled in petroleum processing. The characteristic features of the present invention which are not found in the prior art are the injection of a stream of ethanol jointly with the gasoil feed and the processing of the blend in a catalytic fluid bed under the conditions described in this specification in such way that the resulting gaseous stream has a high ethene content.

The present invention provides for the production of a gaseous stream with an ethene content from 18% to 64% by volume (in respect to the total volume of the feed) by means of the catalytic cracking of liquid hydrocarbons blends containing variable amounts of ethanol (from 0.13 to 50 parts of ethanol per 100 parts by weight of the hydrocarbons), said catalytic cracking reactions being effected through contact of said hydrocarbon blends with granulated catalyst fluid bed.

The cracking reactions, according to the invention herein described, are performed within a temperature range from 430° C. to 550° C. preferably from 480° C. to 520° C., the pressure being in the range from 0 to 5 kg/cm² gauge, preferably from 0 to 2 kg/cm gauge; the temperature within the regeneration zone being from 600° C. to 750° C., preferably between 630° C. and 700° C. in order that the regenerated catalyst when returning to the cracking reactor, will have a heat content sufficient to promote the reaction with the desired yield.

It is another embodiment of the invention that, when the combustion of the carbon deposited on the catalyst particles is not sufficient to raise the temperature of said particles to values between 600° C. and 750° C., the air required for the promotion of the combustion is injected with a certain portion of additional fuel which when burned within the regenerator, will supply a supplementary amount of heat to said particles.

Examples presented below are representative of the present invention but they do not limit the characteristics of the gasoils employed or the shape and capacity of the equipment, though the use of ethanol in defined proportions and operating pressure and temperature are specific conditions of the invention.

Within a pilot reactor, heavy gasoil blends (as specified in Table I) were processed together with commercial ethanol (characteristics thereof are shown in Table II).

TABLE I
CHARACTERISTICS OF THE GASOIL EMPLOYED IN THE EXPERIMENTS

| | |
|---|---|
| Specific gravity | 25.8° API (d 20/4 = 0.8952) |
| Total sulphur = | 1.6% by weight |
| Carbon residue (Ramsbottom) = | 0.28% |
| Aniline point = | 86° C. |
| Pour point = | 33° C. |
| Viscosity at 20° C. = | 19.8 cSt |
| Viscosity at 50° C. = | 10.2 cSt |

TABLE I-continued
CHARACTERISTICS OF THE GASOIL EMPLOYED IN THE EXPERIMENTS

Distillation Curve (ASTM D-1160)

| % volume | °C. |
|---|---|
| IBP | 214 |
| 5 | 313 |
| 10 | 336 |
| 15 | 354 |
| 20 | 367 |
| 25 | 378 |
| 30 | 386 |
| 35 | 394 |
| 40 | 403 |
| 45 | 415 |
| 50 | 424 |
| 55 | 433 |
| 60 | 444 |
| 65 | 456 |
| 70 | 466 |
| 75 | 476 |
| 80 | 486 |
| 85 | 498 |
| 90 | 524 |
| 95 | 532 |
| FBP | 547 |

TABLE II
CHARACTERISTICS OF COMMERCIAL ETHANOL USED IN THE EXPERIMENTS

| | |
|---|---|
| Water content = | 6.25% weight |
| Composition determined by chromatography (on dry basis): | |
| Acetaldehde = | 0.04% weight |
| Acetone = | 0.02% weight |
| Ethanol = | 99.92% weight |
| Non identified substances = | 0.02% weight |

The catalysts used in the described process were selected from four main groups:

1. catalyst formed by an amorphous aluminum silicate of high alumina content whose specifications are shown in Table III;
2. catalyst formed by an amorphous aluminum silicate of low alumina content as specified in Table IV;
3. catalyst formed by a crystalline aluminum silicate (zeolite) of medium activity as described in Table V;
4. catalyst formed by a crystalline aluminum silicate (zeolite) of high activity whose specifications are in Table VI.

TABLE III
Characteristics of an amorphous aluminum silicate catalyst with high alumina content Weight percent composition (by analysis)

| | |
|---|---|
| $Al_2O_3$ | = 27.20% |
| $SiO_2$ | = 69.97% |
| Na | = 0.10% |
| Fe | = 0.30% |

Physical Properties

| | |
|---|---|
| Bulk density | = 0.63 g/cm³ |
| Surface Area | = 136 m²/g |
| Pore Volume | = 0.60 cm³/g |

Granulometric Analysis

| Particle size | % weight |
|---|---|
| less than 53 microns | 0.0 |
| 53–61 microns | 2.0 |
| 61–89 microns | 7.7 |
| 89–124 microns | 20.4 |
| 124–177 microns | 69.9 |
| greater than 177 microns | 0.0 |

TABLE IV

Characteristics of an amorphous aluminum silicate catalyst with low alumina content

| Weight percent composition | |
|---|---|
| Al$_2$O$_3$ | = 15.10% |
| SiO$_2$ | = 81.87% |
| Na | = 0.06% |
| Fe | = 0.54% |
| Physical Properties | |
| Bulk density | = 0.070 g/cm$^3$ |
| Surface area | = 103 m$^2$/g |
| Pore volume | = 0.41 cm$^3$/g |

| Granulometric Analysis | |
|---|---|
| Particle size | % weight |
| 0-20 microns | 0% |
| 0-40 microns | 1% |
| 0-88 microns | 77% |

TABLE V

Characteristics of a crystalline aluminun silicate catalyst (zeolite) of medium activity

| Weight percent composition | |
|---|---|
| Al$_2$O$_3$ | = 34.8% |
| SiO$_2$ | = 62.6% |
| Na | = 0.35% |
| Fe | = 0.25% |
| Physical properties | |
| Bulk density | = 0.77 g/cm$^3$ |
| Surface area | = 105 m$^2$/g |
| Pore volume | = 0.40 cm$^3$/g |

| Granulometric Analysis | |
|---|---|
| Particle size | % weight |
| 0-20 microns | 0 |
| 0-40 microns | 2 |
| 0-80 microns | 58 |

TABLE VI

Characteristics of a crystalline aluminum silicate catalyst (zeolite) of hegh activity

| Weight percent composition | |
|---|---|
| Al$_2$O$_3$ | = 42.00% |
| SiO$_2$ | = 54.18% |
| Na | = 0.38% |
| Fe | = 0.44% |
| Physical properties | |
| Apparent specific gravity | = 0.78g/cm$^3$ |
| Surface area | = 100m$^2$/g |
| Pore volume | = 0.44cm$^3$/g |

| Granulometric Analysis | |
|---|---|
| Particle size | % weight |
| 0-20 microns | 0% |
| 0-40 microns | 1% |
| 0-80 microns | 50% |

Examples 1 to 14 are representative of the use of the various mentioned catalysts and the specific conditions of operation within the range of the physical variables involved in the present invention.

EXAMPLE 1

Ethanol according to the specifications established in Table II and gasoil according to the characteristics shown in Table I were processed in the presence of the catalyst described in Table III (aluminum silicate with high alumina content) in a fluidized bed. The following general conditions were maintained:

| | |
|---|---|
| Ethanol:gasoil ratio | = 0.13:100 |
| Flow of gasoil | = 300g/hour |
| Flow of ethanol | = 0.39gram/hour |
| Reactor temperature | = 500° C.gram/hour |
| Reactor pressure | = 1.07kg/cm$^2$ abs. |
| Space velocity of the reactants | = 3.2 (hour)$^{-1}$ |
| Cantact time of the catalyst with the reactants | = 1.92min |
| Catalyst:reactants ratio | = 9.8g/g |

In the resulting "fuel gas," a yield of 19.5% (by volume) of ethene was obtained.

EXAMPLE 2

The same reacting substances as in Example 1 in the presence of the catalyst described in Table III in a fluidized bed.

The following conditions were maintained:

| | |
|---|---|
| Ethanol:gasoil ratio | = 5:100 |
| Flow of gasoil | = 300 g/h |
| Flow of ethanol | = 15 g/h |
| Reactor temperature | = 500° C. |
| Reactor pressure | = 1.07 kg/cm$^2$ abs. |
| Space velocity | = 3.2 h$^{-1}$ |
| Contact time of the catalyst with the reactants | 32 1.92 min |
| Catalyst:reactants ratio | = 9.8 g/g |

A yield of 39% of ethene (by volume) was obtained in the resulting "fuel gas."

EXAMPLE 3

The same as in Example 1, the same catalyst described in Table III.

Conditions:

| | |
|---|---|
| Ethanol:gasoil ratio | = 10:100 |
| Flow of gasoil | = 300 g/h |
| Flow of ethanol | = 30 g/h |
| Reactor temperature | = 500° C. |
| Reactor pressure | = 1.07 kg/cm$^2$ abs. |
| Space velocity | = 3.5 h$^{-1}$ |
| Contact time | = 1.29 min |
| Catalyst:reactants ratio | = 13.3 g/g |

A yield of 48% of ethene (by volume) was obtained in the resulting "fuel gas."

EXAMPLE 4

As in Example 1, using the same catalyst described in Table III.

Conditions:

| | |
|---|---|
| Ethanol:gasoil ratio | = 30:100 |
| Flow of gasoil | = 300 g/h |
| Flow of ethanol | = 90 g/h |
| Reactor temperature | = 500° C. |
| Reactor pressure | = 1.07 kg/cm$^2$ abs. |
| Space velocity | = 4.15 h$^{-1}$ |
| Contact time | = 1.81 min |
| Catalyst:reactants ratio | = 8.0 g/g |

A yield of 61% (by volume) of ethene was obtained in the resulting "fuel gas."

EXAMPLE 5

As in Example 1, the same catalyst described in Table III was used in a fluidized bed.

Conditions:

| | |
|---|---|
| Ethanol:gasoil ratio | = 50:100 |
| Flow of gasoil | = 300 g/h |
| Flow of ethanol | = 150 g/h |
| Reactor temperature | = 500° C. |
| Reactor pressure | = 1.07 kg/cm$^2$ |
| Space velocity | = 4.79 h$^{-1}$ |
| Contact time | = 2.85 min |
| Catalyst:reactants ratio | = 4.4 g/g |

A yield of 64% of ethene was obtained in the resulting "fuel gas."

EXAMPLE 6

Ethanol according to the specifications given in Table I and gasoil according to the specifications of Table II were processed in the presence of the catalyst described in Table IV (amorphous aluminum silicate with low alumina content)

Conditions:

| | |
|---|---|
| Ethanol:gasoil ratio | = 10:100 |
| Flow of gasoil | = 300 g/h |
| Flow of ethanol | = 30 g/h |
| Reactor temperature | = 480° C. |
| Reactor pressure | = 2.0 kg/cm$^2$ gauge |
| Space velocity | = 3.5 h$^{-1}$ |
| Contact time | = 1.29 min |
| Catalyst:reactants ratio | = 13.3 g/g |

A yield of 40% of ethene (by volume) was obtained in the resulting "fuel gas."

EXAMPLE 7

Ethanol according to the specifications given in Table II and gasoil according to the specifications of Table I were processed in the presence of the catalyst described in Table IV (amorphous aluminum silicate with low alumina content)

Conditions:

| | |
|---|---|
| Ethanol:gasoil ratio | = 10:100 |
| Flow of gasoil | = 300 g/h |
| Flow of ethanol | = 30 g/h |
| Reactor temperature | = 480° C. |
| Reactor pressure | = 1.07 kg/cm$^2$ abs. |
| Space velocity | = 3.5 h$^{-1}$ |
| Contact time | = 1.29 min |
| Catalyst:reactants ratio | = 13.3 g/g |

A yield of 40.4% of ethene (by volume) was obtained in the resulting "fuel gas."

EXAMPLE 8

As in Example 7, except that the new operation conditions are:

| | |
|---|---|
| Ethanol:gasoil ratio | = 10:100 |
| Flow of gasoil | = 300 g/h |
| Flow of ethanol | = 30 g/h |
| Reactor temperature | = 520° C. |
| Reactor pressure | = 2 kg/cm$^2$ gage |
| Space velocity | = 3.5 h$^{-1}$ |
| Contact time | = 1.29 min |
| Catalyst:reactants ratio | = 13.3 g/g |
| Yield of ethene (by volume) in the resulting "fuel gas": 45.5% | |

EXAMPLE 9

Ethanol according to the specifications given in Table II and gasoil according to Table I were processed in the presence of the catalyst described in the Table V, in a fluidized bed. The following conditions were maintained:

| | |
|---|---|
| Ethanol:gasoil ratio | = 10:100 |
| Flow of gasoil | = 300 g/h |
| Flow of ethanol | = 30 g/h |
| Reactor temperature | = 510° C. |
| Reactor pressure | = 2.0 kg/cm$^2$ gage |
| Space velocity of the reactants | = 3.5 h$^{-1}$ |
| Contact time | = 1.29 min |
| Catalyst:reactants ratio | = 13.3 g/g |
| Ethene content in the resulting "fuel gas" | = 49% (by volume) |

EXAMPLE 10

The same reactants and catalyst as in Example 9.

Conditions:

| | |
|---|---|
| Ethanol:gasoil ratio | = 10:100 |
| Flow of gasoil | = 300 g/h |
| Flow of ethanol | = 30 g/h |
| Reactor temperature | = 500° C. |
| Reactor pressure | = 2.0 kg/cm$^2$ gage |
| Space velocity | = 3.5 h$^{-1}$ |
| Contact time | = 1.29 min |
| Ethene content in the resulting "fuel gas" | = 48.5% |

EXAMPLE 11

The same reactants and catalyst as in Example 9.

Conditions:

| | |
|---|---|
| Ethanol:gasoil ratio | = 10:100 |
| Flow of gasoil | = 300 g/h |
| Flow of ethanol | = 30 g/h |
| Reactor temperature | = 520° C. |
| Reactor pressure | = 1.07 kg/cm$^2$ gage |
| Space velocity | = 3.5 h$^{-1}$ |
| Contact time | = 1.29 min |
| Catalyst:reactants ratio | = 13.3 g/g |
| Ethene content in the "fuel gas" | = 49.7% |

EXAMPLE 12

Ethanol according to Table II and gasoil according to Table I were processed in the presence of the catalyst described in Table VI in a fluidized bed. The following conditions were maintained:

| | |
|---|---|
| Ethanol:gasoil ratio | = 10:100 |
| Flow of gasoil | = 300 g/h |
| Flow of ethanol | = 30 g/h |
| Reactor temperature | = 520° C. |
| Reactor pressure | = 1.07 kg/cm$^2$ abs. |
| Space velocity of the reactants | = 3.5 h$^{-1}$ |
| Contact of catalyst with the reactants | = 1.29 min |
| Catalyst:reactants ratio | = 13.3 g/g |
| Ethene content in the "fuel gas" | = 52% (by volume) |

EXAMPLE 13

Reactants and catalyst as in Example 12.
Conditions:

| | |
|---|---|
| Ethanol:gasoil ratio | = 10:100 |
| Flow of gasoil | = 300 g/h |
| Flow of ethanol | = 30 g/h |
| Reactor temperature | = 520° C. |
| Reactor pressure | = 2.0 kg/cm$^2$ gage |
| Space velocity | = 3.5 h$^{-1}$ |
| Contact time | = 1.29 min |
| Catalyst:reactants ratio | = 13.3 g/g |
| Ethene content in the resulting "fuel gas" | = 51.5% (by volume) |

EXAMPLE 14

Reactants and catalyst as in Example 13
Conditions:

| | |
|---|---|
| Ethanol:gasoil ratio | = 10:100 |
| Flow of gasoil | = 300 g/h |
| Flow of ethanol | = 30 g/h |
| Reactor temperature | = 480° C. |
| Reactor pressure | = 1.07 kg/cm$^2$ abs. |
| Space velocity | = 3.5 h$^{-1}$ |
| Contact time | = 1.29 min |
| Catalyst:reactants ratio | = 13.3 g/g |
| Ethene content in the resulting "fuel gas" | = 50.6% |

In Examples 4 and 5, as the quantity of carbon deposited over the catalyst particles was lower than in other examples and, as a consequence, its combustion in the regenerator would not produce enough heat to maintain the temperature between 600° C. and 750° C., a stream of hydrocarbons with one and two carbon atoms was added to the air stream introduced to provide combustion, thus the said expected temperature range could be reached. It is easily understood by those skilled in the art that many different kinds of petroleum derivatives may be employed as auxiliary fluid in the combustion of the carbon layer over the catalyst particles. Examples of such combustibles mixtures are gaseous hydrocarbon mixtures or sprayed liquid blends.

What we claim is:

1. A process for obtaining gaseous streams containing from 18.8 percent to 64 percent by volume ethene, said process comprising the steps of
   (a) admixing ethanol and hydrocarbons selected from the group consisting of gasoils and heavier petroleum cuts suitable for cracking to form a blend containing 0.13 to 50 parts by weight ethanol per 100 parts by weight of said hydrocarbons; and
   (b) contacting said admixture with a granulated cracking catalyst in a fluidized bed at a temperature between 430° C. and 550° C. and under a pressure from 0 to 5 kg/cm$^2$ gauge to yield a gaseous stream containing from 18.8 percent to 64 percent by volume ethene.

2. A process according to claim 1 wherein said hydrocarbons are high boiling petroleum fractions.

3. A process according to claim 1, wherein said hydrocarbons boil within a temperature range of from 200° C. to 600° C.

4. A process according to claim 1, wherein said temperature is from 480° C. to 520° C.

5. A process according to claim 1, wherein said pressure is from 0 to 2 kg/cm$^2$ gauge.

6. A process according to claim 1 comprising the additional step of regenerating said cracking catalyst.

7. A process according to claim 6 wherein said cracking catalyst is granulated aluminum silicate and said regeneration comprises contacting said catalyst with a mixture of air and hydrocarbons at a temperature of from 600° C. to 750° C.

8. A process for obtaining a gaseous stream containing from 18.8% to 64% by volume ethene comprising the following steps:
   (a) forming a blend containing ethanol in the ratio of 0.13 to 50 parts by weight per 100 parts by weight of high boiling petroleum fractions;
   (b) contacting said blend of high boiling petroleum fractions and ethanol with a granulated aluminum silicate catalyst in a fluidized bed at a temperature between 430° C. and 550° C. and under 0 to 5 kg/cm$^2$ gauge pressure;
   (c) during the reaction, as the catalyst particles become coated with a carbon layer, sending said particles to a reactor and there contacting them with a mixture of air and hydrocarbons, burning said mixture and the carbon layer on the catalyst particles in a fluidized bed in such a way that said catalyst particles are rendered free of the carbon layer and heated to a temperature between 600° C. and 700° C.; and
   (d) returning the catalyst particles free of the carbon layer to the mixture of high boiling petroleum fractions and ethanol, the heat content of said particles being sufficient to maintain the thermal conditions of the cracking reaction.

9. A process for obtaining gaseous streams rich in ethene according to claim 8 wherein the high boiling petroleum fractions boil within a temperature range of from 200° C. to 600° C.

10. A process according to claim 8 wherein the contact between the catalyst and the blend of high boiling petroleum fractions with ethanol is performed in the temperature range from 480° C. to 520° C.

11. A process according to claim 8 wherein the contacting of the catalyst with the high boiling petroleum fractions-ethanol blend is performed under 0 to 2 kg/cm$^2$ gauge pressure.

12. A process for obtaining gaseous streams rich in ethene according to claim 8 wherein, after the combustion of the carbon deposited over the catalyst particles, the temperature of said particles is in the range of from 630° C. to 700° C.

13. A process according to claim 8 wherein the granulated catalyst is an amorphous aluminum silicate with high alumina content.

14. A process according to claim 8 wherein the granulated catalyst is an amorphous aluminum silicate with low alumina content.

15. A process according to claim 8 wherein the granulated catalyst is a crystalline aluminum silicate.

* * * * *